United States Patent [19]

Brockhaus et al.

[11] 4,396,776

[45] Aug. 2, 1983

[54] PROCESS FOR THE PRODUCTION OF METHYL-BLOCKED ETHOXYLATES

[75] Inventors: Rudolf Brockhaus, Marl; Hans-Jürgen Franke, Dorsten, both of Fed. Rep. of Germany

[73] Assignee: Chemische Werke Huels, Aktiengesellschaft, Marl, Fed. Rep. of Germany

[21] Appl. No.: 279,632

[22] Filed: Jul. 2, 1981

[30] Foreign Application Priority Data

Jul. 3, 1980 [DE] Fed. Rep. of Germany ....... 3025190

[51] Int. Cl.$^3$ ................. C07C 91/40; C07C 91/42; C07C 43/11; C07C 43/18
[52] U.S. Cl. ................................. 564/443; 564/505; 568/608; 568/613; 568/621
[58] Field of Search ................. 568/608, 613, 621; 564/505, 443

[56] References Cited

U.S. PATENT DOCUMENTS 3,428,692  2/1969  Starks et al. ...................... 568/621

Primary Examiner—John Doll
Attorney, Agent, or Firm—Millen & White

[57] ABSTRACT

A process for preparing a methyl-blocked ethoxylate comprises heating at 180°–320° C., in the presence of a catalytically effective amount of a noble metal catalyst, an unsubstituted ethoxylate of 3 or more ethoxy units, or a monoalkyl-, monoaryl-, mono- or di-alkylamino- or mono- or di-arylamino ethoxylate of 2 or more ethoxy units, or a monoalkyl- or monoaryl-N,N-bis(ethoxylate) of 2 or more ethoxy units, all of which are derived from vicinal glycols, whereby there is prepared a corresponding methyl-blocked ethoxylate product which, for an unsubstituted ethoxylate starting material is a dimethylethoxylate having two fewer ethoxy units than the starting ethoxylate, and for the other ethoxylate starting materials, is a methylethoxylate having one less ethoxy unit in each ethoxylate group of the starting material.

8 Claims, No Drawings

PROCESS FOR THE PRODUCTION OF METHYL-BLOCKED ETHOXYLATES

BACKGROUND OF THE INVENTION

Monoalkyl or monoaryl ethoxylates, i.e., the monoalkyl or monoaryl ethers of polyglycols, can be readily prepared, as can be the ethoxylates, themselves, i.e., the polyglycols. They are produced industrially from alcohols or phenols, respectively, and ethylene oxide. Using ethylene oxide and propylene oxide, mixed ether chains are also prepared. The properties of these compounds depend on the structure of the end-positioned alcohol, on the number of ethoxy or propoxy groups attached by condensation, and, for the polyglycols, on the molecular weight.

Because of the relationship of their properties to the requirements of the end use, such polyglycols and their monoethers are suitable, as nonionic tensides, solvents for gas scrubbing, hydraulic fluids, etc. However, their terminal OH-groups impart a certain instability, for example with respect to oxidation. This disadvantage is not exhibited by the dialkyl ethers. However, unlike the polyglycols (1,2-glycols) and their monoalkyl ethers whose preparations are easy and modifiable, the manufacture of the dialkyl ethers presents difficulties.

Dialkyl ethoxylates can be obtained, for example, by reacting monoalkyl ethoxylates with isobutene, yielding a tert-butyl alkyl ethoxylate. In the same way, the methyl ethers can be obtained according to classical methods, such as by reacting the sodium alcoholate with halogenated hydrocarbons. However, these manufacturing methods are very expensive.

It is known from U.S. Pat. No. 3,428,692 whose disclosure is incorporated by reference herein, to produce methyl ethers, namely the methyl-blocked ethoxylates, by heating ethoxylates consisting of vicinal glycols, or the monoalkyl or monophenyl ethers thereof, to 200°–300° C. in the presence of nickel or cobalt catalysts, preferably Raney nickel, by means of deformylation. However, in this process, mixtures are produced consisting of the desired methyl ethers and incompletely reacted ethoxylates and unidentified aldehydes, in accordance with the following reaction scheme:

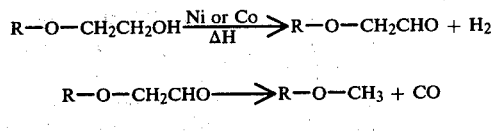

Consequently, there is a continuing great interest in producing these monoalkyl or monoaryl methylethoxylates and dimethylethoxylates selectively and in high yields.

SUMMARY OF THE INVENTION

Accordingly, it is an object of this invention to provide such a process for preparing such methyl blocked ethoxylates which are free from the mentioned disadvantages.

Upon further study of the specification and appended claims, further objects and advantages of this invention will become apparent to those skilled in the art.

These objects have been attained by providing a process for the production of methyl-blocked ethoxylates, such as monoalkyl-, monoaryl-, mono- or di- alkylamino- or -arylamino- methylethoxylates and such as dimethylethoxylates, by heating from ethoxylates or monoalkyl, monoaryl, mono- or di- alkylamino- or -arylamino- ethoxylates, constructed from vicinal glycols, in the presence of catalysts, wherein ethoxylates with 3 or more ethoxy groups or alkyl-, aryl-, mono- or di- alkylamino- or -arylamino- ethoxylates with two or more ethoxy groups are heated to 180°–320° C. in the presence of noble metal catalysts, such as palladium, platinum, or rhodium catalysts.

That is, this invention provides a process for preparing a methyl-blocked ethoxylate comprising heating at 180°–320° C., in the presence of a catalytically effective amount of a noble metal catalyst, an unsubstituted ethoxylate of 3 or more ethoxy units, or a monoalkyl-, monoaryl-, mono- or di- alkylamino- or mono- or di- arylamino ethoxylate of 2 or more ethoxy units, or a monoalkyl- or monoaryl-N,N-bis(ethoxylate) of 2 or more ethoxy units, all of which are derived from vicinal glycols, whereby there is prepared a corresponding methyl-blocked ethoxylate product which, for the unsubstituted ethoxylate starting materials is a dimethylethoxylate, having two fewer ethoxy units than the starting ethoxylate and for the other ethoxylate starting materials, is a methylethoxylate, having one less ethoxy unit in each ethoxylate group or the starting material.

DETAILED DISCUSSION

Surprisingly, the methyl-blocked ethoxylates, such as the monoalkyl- or monoaryl- methylethoxylates and dimethylethoxylates are obtained selectively in almost quantitative yields in accordance with this invention by heating the corresponding ethoxylates, the alkyl- or arylethoxylates or the mono- or di- alkylamino- or arylaminoethoxylates in the presence of the noble metal catalysts to 180°–320° C. Even in cases of incomplete conversion, practically no aldehyde is formed. From ethoxylates, dimethylethoxylates are obtained having a molecular weight lowered by 2 HCHO groups (or 2 $H_2 + 2$ CO); and from monoalkyl ethoxylates or from the corresponding monoaryl-, mono- or di- alkylamino or mono- or di- arylamino derivatives, the corresponding monoalkyl (or aryl, alkylamino or arylamino) methylethoxylates are obtained having a molecular weight lowered by 1 HCHO group (or $H_2 + CO$).

Suitable (non-etherified) ethoxylates include those of 3 or more (e.g., up to 20) ethoxy groups, such as triethylene glycol (triglycol) as well as the higher-molecular weight ethoxylates. These ethoxylates generally involve products which are not entirely uniform. For example, an ethoxylate with 8 ethoxy groups has 8 ethoxy groups on the average, but also partially contains moieties of 6 and 7 as well as 9 and 10 ethoxy groups. Besides the pure ethoxylates, equivalent for use in this invention are mixed ethoxylate-propoxylates built up from ethylene oxide and propylene oxide. Such diglycols are only partially reacted to from the corresponding methyl glycol; they react partially by ring closure and splitting off of water to form dioxanes.

Suitable monoalkyl (e.g., 1–22 C atoms) or monoaryl (e.g., of 6–24 C atoms) ethoxylates with two or more (e.g., up to 20) ethoxy groups, include for example, monomethyl-, monoethyl-, monopropyl-, monobutyl-, monohexyl-, monooctyl-, monolauryl-, monophenyl-, monoalkylphenylethoxylates, etc. Suitable monoalkylamino, di-alkylamino, mono-arylamino and di-arylamino ethoxylates with two or more (e.g., up to 30) ethoxy groups include, for example, methylamino-, dimethylamino-, ethylamino-, diethylamino-, butylamino-, laurylamino-, anilino-, methylanilno- ethoxylates, etc. Also included are the corresponding mono(alkyl or aryl)-N,N-bis(ethoxylates).

Tert-monoalkyl ethoxylates and tert-monoalkylamino- ethoxylates are less suitable, since they tend to decompose.

Suitable noble metal catalysts include palladium, platinum and rhodium catalysts, as well as mixtures thereof. Because of the scarcity of nobel metals, however, noble metal catalysts applied to supports are preferably employed. Very good results are attained with palladium, platinum, or rhodium on $Al_2O_3$ and/or $SiO_2$, carborundum, or activated carbon as the supports. The supports generally contain 0.1–1% by weight of noble metal. Palladium catalysts are preferred. Generally, 0.02–10 wt. % of noble metal based on the amount of ethoxylate is employed. Other suitable noble metal catalysts include silver and gold.

The reaction on the noble metal catalysts takes place at temperatures of 180°–320° C., preferably 210°–310° C., especially 240°–300° C. Higher temperatures lead to cracking of the molecules whereby very nonuniform reaction products are formed, and the catalyst loses its activity. The reaction is generally conducted under normal pressure, but it is also possible to operate in the subatmospheric and superatmospheric ranges. Pressures generally are 0.4–20 atm. The reaction can be conducted batchwise or continuously. An inert gas stream can be used for circulation purposes.

The reaction time depends on the reaction temperature and the ratio of reactant to catalyst. Batchwise, times usually are 5–50 hours. Space-time yields of about 40–200 g/l of catalyst ● hour are obtained. In the presence of palladium catalysts, space-time yields of 80–200 g/l of catalyst ● hour are obtained.

The process of this invention is of special economy for the reaction of lowly volatile or nonvolatile production residues obtained in the ethoxylate synthesis, for example for reaction of the mono- ethylethoxylate residue (monoethyl polyglycol ether residue). This product can be converted in accordance with this invention into distillable ethylmethylethoxylates.

The methyl-blocked ethoxylates obtained according to this invention are preferably utilized as hydraulic fluids, for example as brake fluid. They are furthermore used as nonionic tensides having an especially high resistance to atmospheric oxygen.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Reaction of ethyl diglycol (an ethylethoxylate) to form ethyl methyl glycol (an ethylmethylethoxylate).

A tube having a diameter of 32 mm. and a height of 80 cm. serves as the reactor. The reactor is filled with 600 ml. of a supported catalyst of 0.5% Pd on an $Al_2O_3$ support, grain size 3–5 mm. By means of a pump, 69 g. ethyl diglycol, preheated to the reaction temperature, is introduced per hour. The reaction temperature is maintained at 225°–230° C., the operating pressure of 5 bar.

With an ethyl diglycol conversion of > 99% (OH-number in the reaction product: 1.8), 52.4 g/h of ethyl methyl glycol is obtained, corresponding to a space-time yield of 87.3 g. of ethyl methyl glycol/liter of catalyst ● hour.

EXAMPLE 2

Reaction of butyl diglycol (a butylethoxylate) to from butyl methyl glycol (a butylmethylethoxylate).

In a 1-liter round-flask reactor, 200 ml. of a supported catalyst is provided, consisting of 0.5% Pt on an $Al_2O_3$ support, grain size 3–5 mm. To this is added 400 g. of butyl diglycol. By the introduction of an inert gas stream of about 2 l/h, the charge is continuously slightly circulated.

The reaction temperature is maintained at 190°–215° C., the pressure at 1 bar. A gaseous mixture of hydrogen, carbon monoxide, and inert gas escapes constantly. With a butyl diglycol conversion of about 45% (OH-number in the reaction product: 208), an aldehyde proportion prevails of 0.8% (CO-number: 2.8). After 36 hours, the butyl diglycol conversion is > 99% (OH-number in the reaction product: 2.7). With a yield of 321 g. of butyl methyl glycol, the efficacy of the catalyst is 44.6 g. of butyl methyl glycol/l of catalyst ● hour.

EXAMPLE 3

Reaction of phenyl diglycol ether (a phenylethoxylate) to form methyl phenyl glycol (a methylphenylethoxylate).

The reactor is the same as described in Example 1. However, 600 ml of a supported catalyst is utilized, 0.5% Rh on a $SiO_2$ support, grain size 3–5 mm. By way of a pump, 30.1 g per hour of phenyl diglycol ether is introduced. The reaction temperature is maintained at 280° C., the operating pressure at 1.5 bar. In this process, the phenyl diglycol conversion is > 99% (OH-number in the reaction product: 3.1). The reaction product contains 24.6 g/h of methyl phenyl glycol. This corresponds to a space-time yield of 41.1 g of methyl phenyl glycol/l of catalyst ● hour.

EXAMPLE 4

Reaction of laurylethoxylate (on the average 8 Eo) to form laurylmethylethoxylate (lauryl heptaglycol methyl ether).

In a 1-liter round-flask reactor, 250 ml of the catalyst is provided as described in Example 1, as well as 500 g of laurylethoxylate (8 Eo). By the introduction of ~2 l/h of inert gas, the charge is constantly slightly circulated. With a reaction temperature of 240°–250° C. and under normal pressure, the laurylethoxylate conversion after 11 hours is > 99% (OH-number in the reaction product: 0.9). The yield of 467 g of lauryl methyl heptaglycol corresponds to a space-time yield of 169.8 g of lauryl methyl heptaglycol/l of catalyst ● hour.

EXAMPLE 5

Reaction of the boiling residue obtained in the ethoxylate synthesis of butylethoxylate (on the average 5 Eo, butyl polyglycol ether) to form butyl methyl tetraglycol.

The reactor and catalyst are the same as described in Example 1. By way of a pump, 92 g per hour of boiling residue is introduced. The reaction temperature is maintained at about 300° C., the operating pressure at 1.5 bar. In this process, a butyl polyglycol ether conversion is obtained of > 99% (OH-number in the reaction product: 2). In the gaseous reactor discharge, traces of methane are found in addition to hydrogen and carbon monoxide. The yield of 80.4 g/h of butyl methyl tetraglycol corresponds to a space-time yield of 134 g of butyl methyl tetraglycol/l of catalyst • hour.

EXAMPLE 6

Reaction of the boiling residue obtained in the ethoxylate synthesis of ethyl tetraglycol ether (ethylethoxylate, on the average 4 Eo) to form ethyl methyl triglycol.

The reactor and catalyst are the same as described in Example 1. By way of a pump, 84 g per hour of boiling residue is introduced. The reaction temperature is maintained at about 300° C., the operating pressure at 1.5 bar. In this way, an ethyl tetraglycol ether conversion is achieved of > 99% (OH-number in the reaction product: 2.3). The reaction product contains 70.8 g of ethyl methyl triglycol, corresponding to a space-time yield of 118 g of ethyl methyl triglycol/l of catalyst • hour.

EXAMPLE 7

Reaction of N,N-bis(tetraethoxylate) tallow fatty amine,

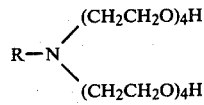

to form N,N-bis(methyl triglycol) tallow fatty amine.

A 1-liter round-flask reactor is charged with 250 ml of the catalyst described in Example 1 and 500 g of N,N-bis(tetraethoxylate) tallow fatty amine. At a reaction temperature of 245° C. and under normal pressure, the charge is continuously slightly circulated by introducing 2 l/h of an inert gas. After 14 hours, N,N-bis(tetraethoxylate) tallow fatty amine conversion is > 99% (OH-number in the reaction product: < 1). The yield is 445 g of N,N-bis(methyl triglycol) tallow fatty amine, corresponding to a catalyst efficacy of 127 g of N,N-bis(methyl triglycol) tallow fatty amine/l of catalyst • hour.

EXAMPLE 8

Reaction of tetraglycol (an ethoxylate) to dimethyl diglycol (a dimethylethoxylate).

The reactor and catalyst are the same as described in Example 1. By way of a pump, 120 g of tetraglycol per hour is introduced. The reaction temperature is maintained at 275° C., the operating pressure at 1.5 bar.

With a tetraglycol conversion of > 99% (OH-number in the reaction product: 2.8), 81.9 g/h of dimethyl diglycol is obtained, corresponding to a space-time yield of 136.5 g of dimethyl diglycol/l of catalyst • hour.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a methyl-blocked ethoxylate comprising heating at 180°–320° C., in the presence of a catalytically effective amount of a noble metal catalyst, an unsubstituted ethoxylate of 3 or more ethoxy units, or a monoalkyl-, monoaryl-, mono- or dialkylamino or mono- or di-arylamino ethoxylate of 2 or more ethoxy units, or a monoalkyl- or monoaryl-N,N-bis(ethoxylate) of 2 or more ethoxy units, whereby there is prepared a corresponding methyl-blocked ethoxylate product which, for an unsubstituted ethoxylate starting material is a dimethyl-ethoxylate having two fewer ethoxy units than the starting ethoxylate, and for the other ethoxylate starting materials is a methylethoxylate having one less ethoxy unit in each ethoxylate group of the starting material.

2. A process of claim 1, wherein the noble metal catalyst is palladium, platinum, rhodium, silver or gold.

3. A process of claim 2, wherein the catalyst is applied to a support.

4. A process of claim 3, wherein the catalyst supports is $Al_2O_3$, $SiO_2$, carborundum or activated carbon.

5. A process of claim 3, wherein the catalyst support is $Al_2O_3$ or $SiO_2$.

6. A process of claim 1 or 5, wherein the noble metal catalyst is palladium.

7. A process of claim 3, wherein the amount of catalyst on the support is 0.1 to 1% by weight.

8. A process of claim 1, wherein the reaction temperature is 240°–300° C.

* * * * *